United States Patent
Matsuoka et al.

(10) Patent No.: US 11,054,433 B2
(45) Date of Patent: Jul. 6, 2021

(54) AUTOMATED ANALYZER AND CONTROL METHOD FOR SAME

(71) Applicant: Hitachi High-Tech Corporation, Tokyo (JP)

(72) Inventors: Yuya Matsuoka, Tokyo (JP); Akihisa Makino, Tokyo (JP); Hajime Yamazaki, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 231 days.

(21) Appl. No.: 15/781,530

(22) PCT Filed: Dec. 2, 2016

(86) PCT No.: PCT/JP2016/085843
§ 371 (c)(1),
(2) Date: Jun. 5, 2018

(87) PCT Pub. No.: WO2017/122455
PCT Pub. Date: Jul. 20, 2017

(65) Prior Publication Data
US 2018/0275155 A1 Sep. 27, 2018

(30) Foreign Application Priority Data
Jan. 13, 2016 (JP) .............................. JP2016-004721

(51) Int. Cl.
*G01N 35/02* (2006.01)
*G01N 35/10* (2006.01)
(Continued)

(52) U.S. Cl.
CPC ........... *G01N 35/025* (2013.01); *G01N 35/00* (2013.01); *G01N 35/0092* (2013.01);
(Continued)

(58) Field of Classification Search
CPC ...... G01N 35/025; G01N 35/02; G01N 35/00; G01N 35/0092; G01N 35/026;
(Continued)

(56) References Cited

U.S. PATENT DOCUMENTS 5,855,847 A   1/1999  Oonuma et al.
6,440,369 B1  8/2002  Oonuma et al.
(Continued)

FOREIGN PATENT DOCUMENTS

CN   1133438 A   10/1996
CN   1154476 A   7/1997
(Continued)

OTHER PUBLICATIONS

International Search Report (PCT/ISA/210) issued in PCT Application No. PCT/JP2016/085843 dated Feb. 21, 2017 with English translation (four (4) pages).
(Continued)

*Primary Examiner* — Kathryn Wright
*Assistant Examiner* — Curtis A Thompson
(74) *Attorney, Agent, or Firm* — Crowell & Moring LLP

(57) ABSTRACT

An automated analyzer has a reaction disk on which a plurality of reaction vessels capable of holding sample and reagent mixtures can be placed, a first cover for covering at least a portion of the area above the reaction disk, a second cover that can be opened and closed independently from the first cover, at least one sensor for monitoring the opening and closing of the first cover, and a control unit for monitoring a signal from the sensor and carrying out control such that if the first cover has not been opened and closed during the period until a new analysis operation is started, a pre-analysis cleaning operation, blank measurement operation, or both, are skipped.

13 Claims, 9 Drawing Sheets

(51) Int. Cl.
  *G01N 35/00* (2006.01)
  *G01N 35/04* (2006.01)
  *G01N 21/01* (2006.01)
  *G01N 33/86* (2006.01)
  *G01N 33/48* (2006.01)
  *G01N 1/00* (2006.01)

(52) U.S. Cl.
  CPC ........... *G01N 35/02* (2013.01); *G01N 35/026* (2013.01); *G01N 35/1004* (2013.01); *G01N 1/00* (2013.01); *G01N 21/01* (2013.01); *G01N 33/48* (2013.01); *G01N 33/86* (2013.01); *G01N 35/10* (2013.01); *G01N 35/1002* (2013.01); *G01N 2035/00316* (2013.01); *G01N 2035/0437* (2013.01)

(58) Field of Classification Search
  CPC ...... G01N 35/1004; G01N 33/48; G01N 1/00; G01N 21/01; G01N 33/86; G01N 35/10; G01N 35/1002; G01N 2035/0437; G01N 2035/00316
  See application file for complete search history.

(56) References Cited

U.S. PATENT DOCUMENTS

| | | | |
|---|---|---|---|
| 2002/0025275 A1 | 2/2002 | Oonuma et al. | |
| 2009/0035182 A1* | 2/2009 | Soma | G01N 35/00693 422/82.05 |
| 2011/0020948 A1* | 1/2011 | Yamato | G01N 35/0092 436/174 |
| 2014/0202828 A1* | 7/2014 | Ishigami | G01N 35/1009 198/340 |
| 2014/0241945 A1* | 8/2014 | Oonuma | G01N 35/025 422/64 |
| 2015/0104351 A1* | 4/2015 | Makino | G01N 35/0092 422/64 |

FOREIGN PATENT DOCUMENTS

| | | |
|---|---|---|
| CN | 101358986 A | 2/2009 |
| CN | 101963621 A | 2/2011 |
| CN | 103842826 A | 6/2014 |
| EP | 2 023 147 A2 | 2/2009 |
| EP | 2 278 336 A2 | 1/2011 |
| EP | 2 762 889 A1 | 8/2014 |
| JP | 60-25964 U | 2/1985 |
| JP | 5-240866 A | 9/1993 |
| JP | 9-96640 A | 4/1997 |
| JP | 11-23580 A | 1/1999 |
| JP | 2009-31202 A | 2/2009 |
| JP | 2010-216889 A | 9/2010 |
| JP | 2013-72799 A | 4/2013 |
| WO | WO 2013-187210 A1 | 12/2013 |

OTHER PUBLICATIONS

Japanese-language Written Opinion (PCT/ISA/237) issued in PCT Appliation No. PCT/JP2016/085843 dated Feb. 21, 2017 (six (6) pages).
Extended European Search Report issued in counterpart European Application No. 16885058.4 dated Oct. 1, 2019 (eleven pages).
Chinese-language Office Action issued in Chinese Application No. 201680070155.X dated Jul. 17, 2020 with English translation (18 pages).

* cited by examiner

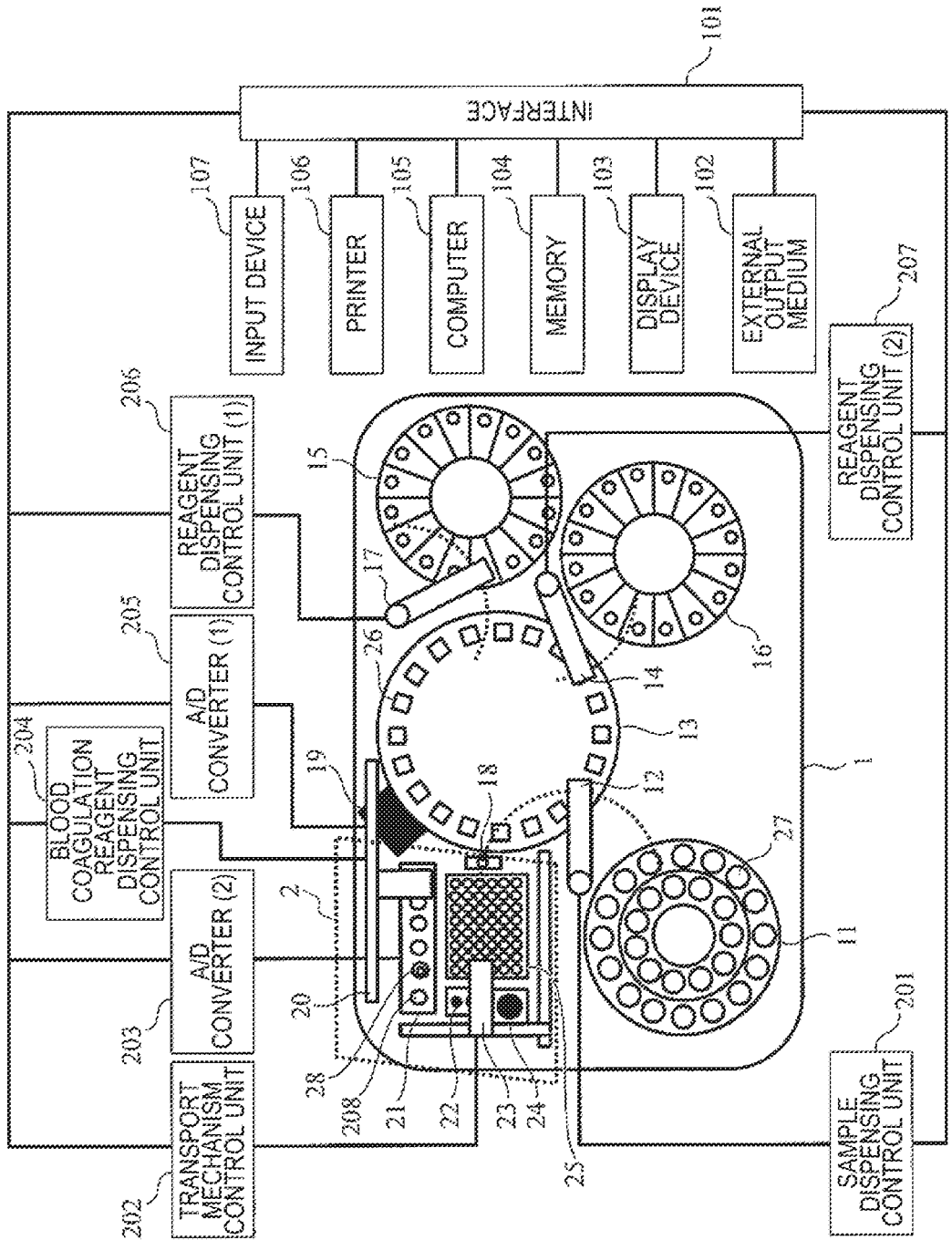
[FIG. 1]

[FIG. 2]
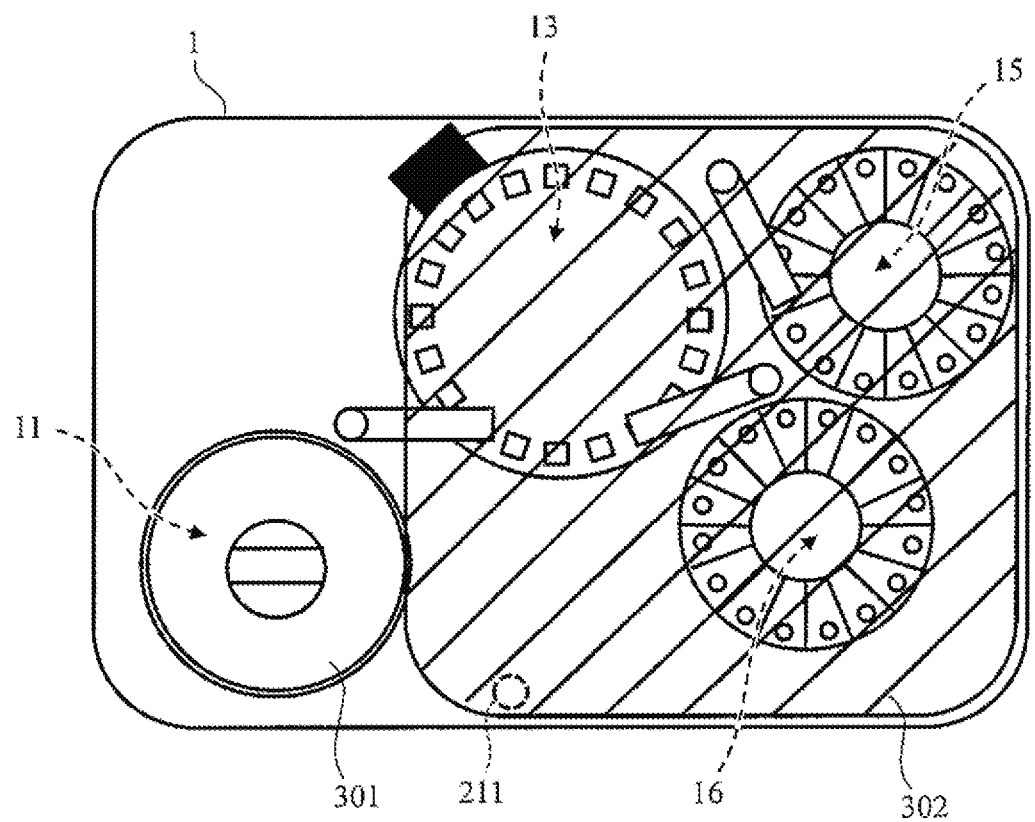

[FIG. 3]
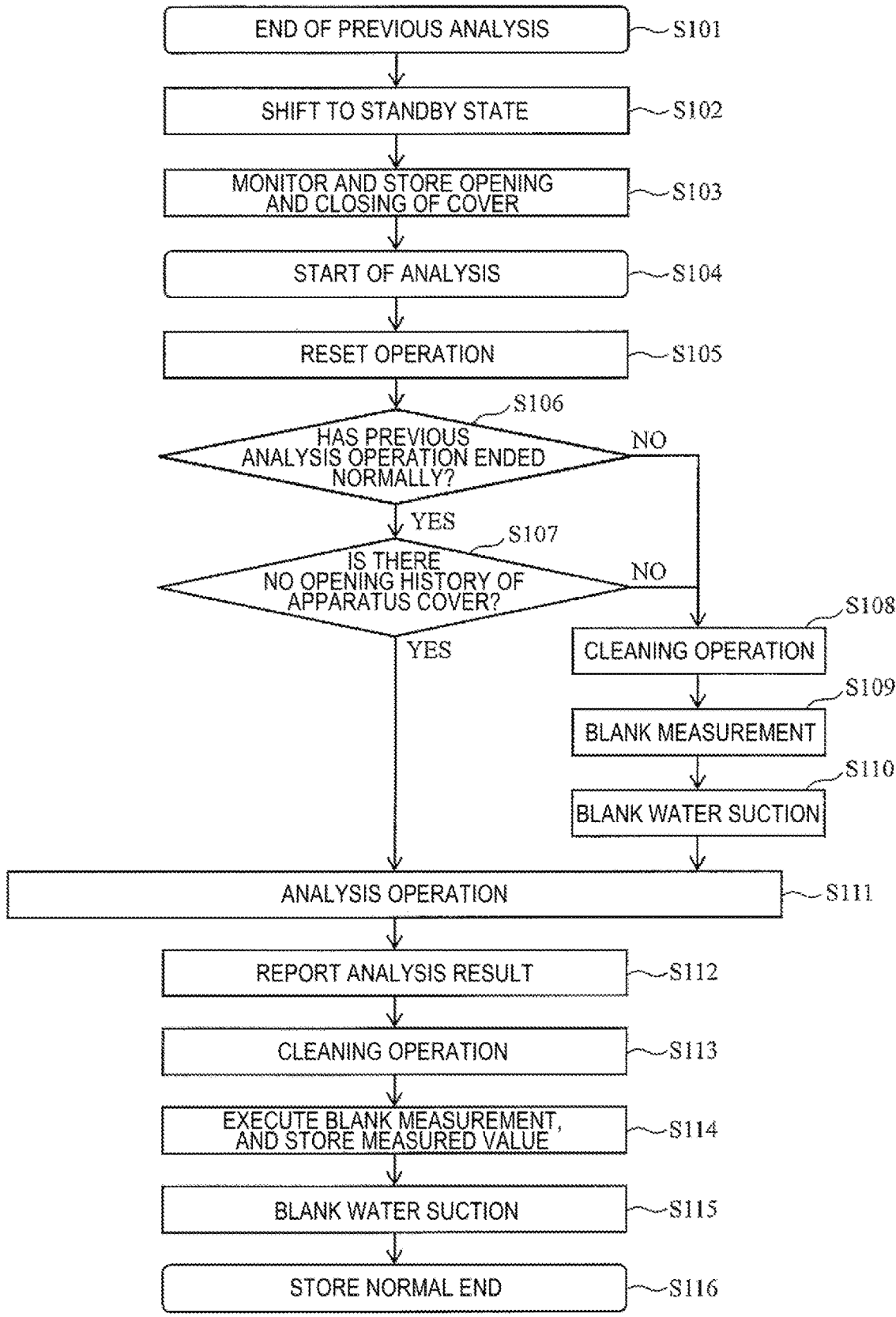

[FIG. 4]
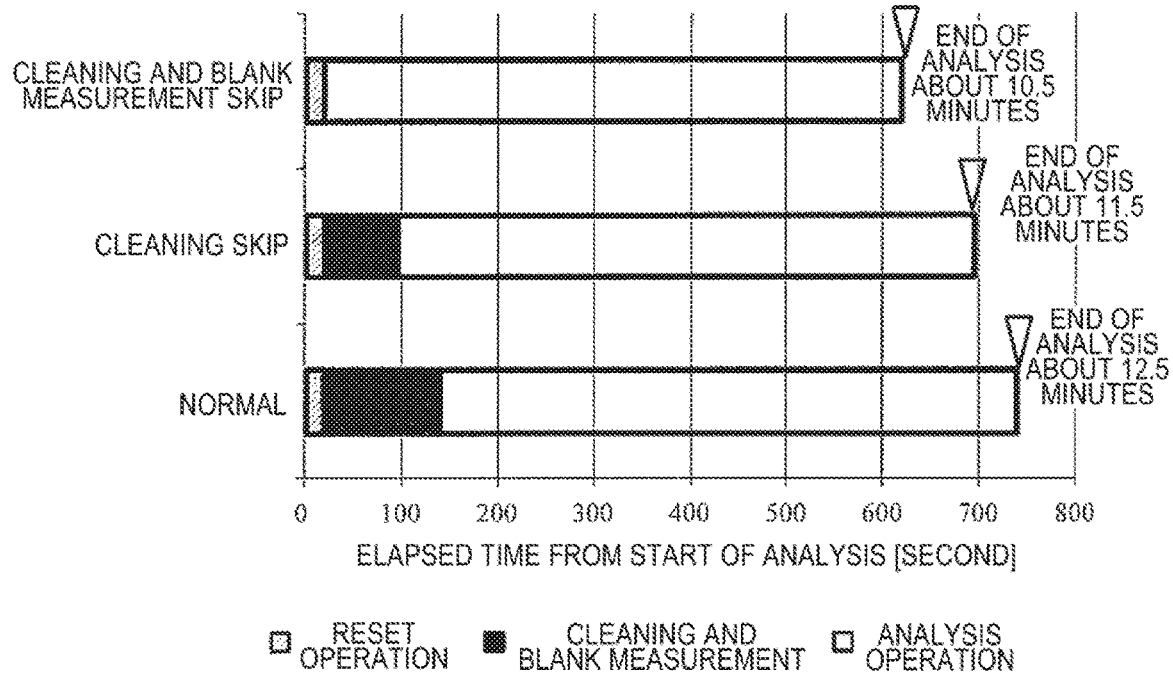
[FIG. 5]
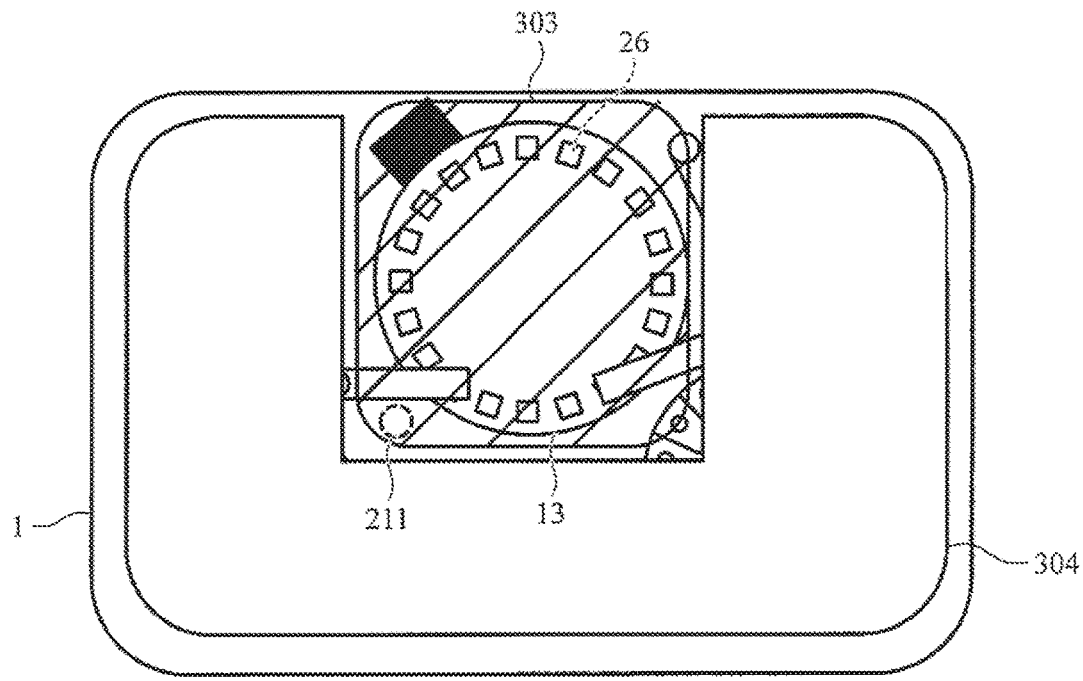

[FIG. 6]
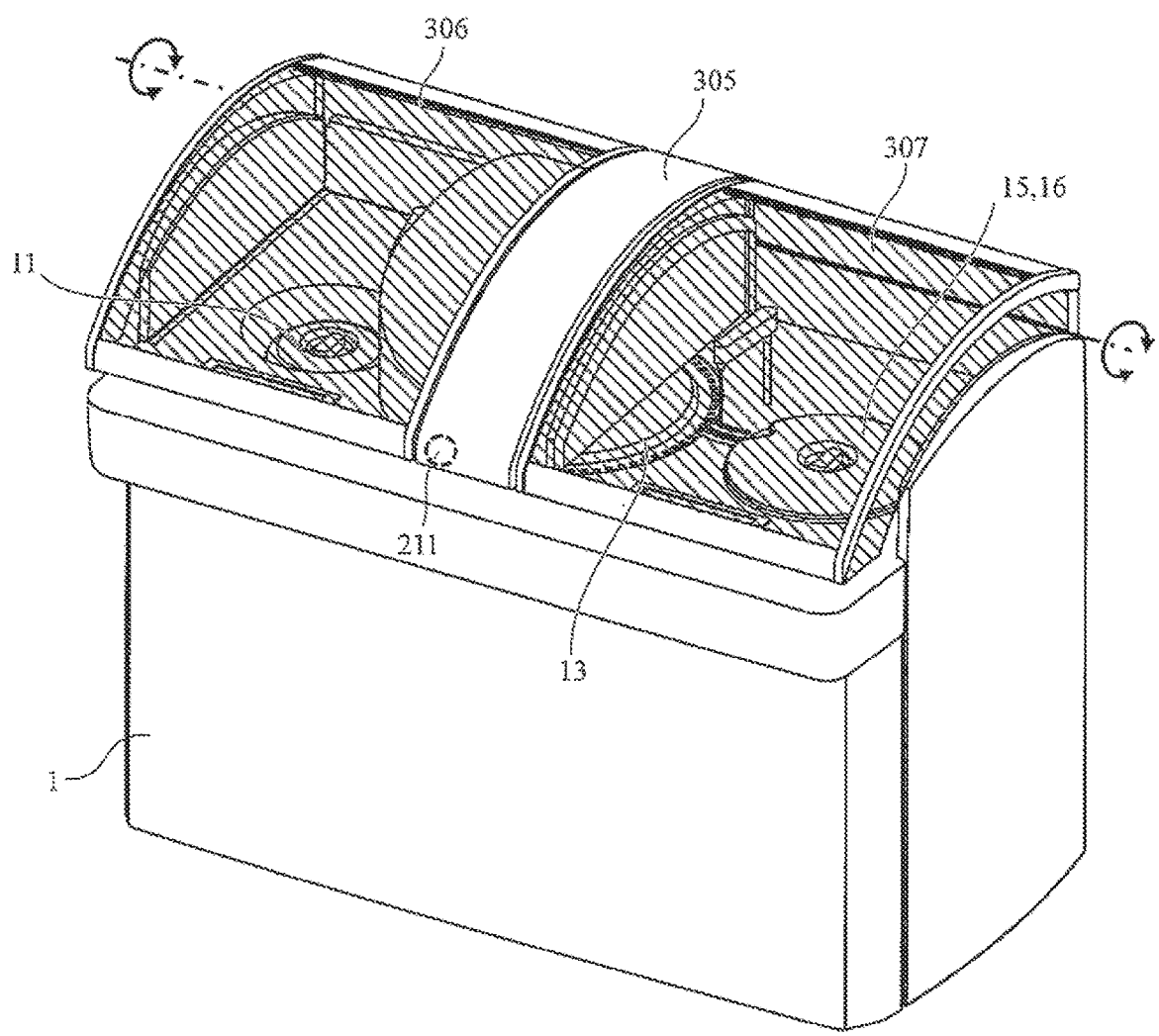

[FIG. 7]
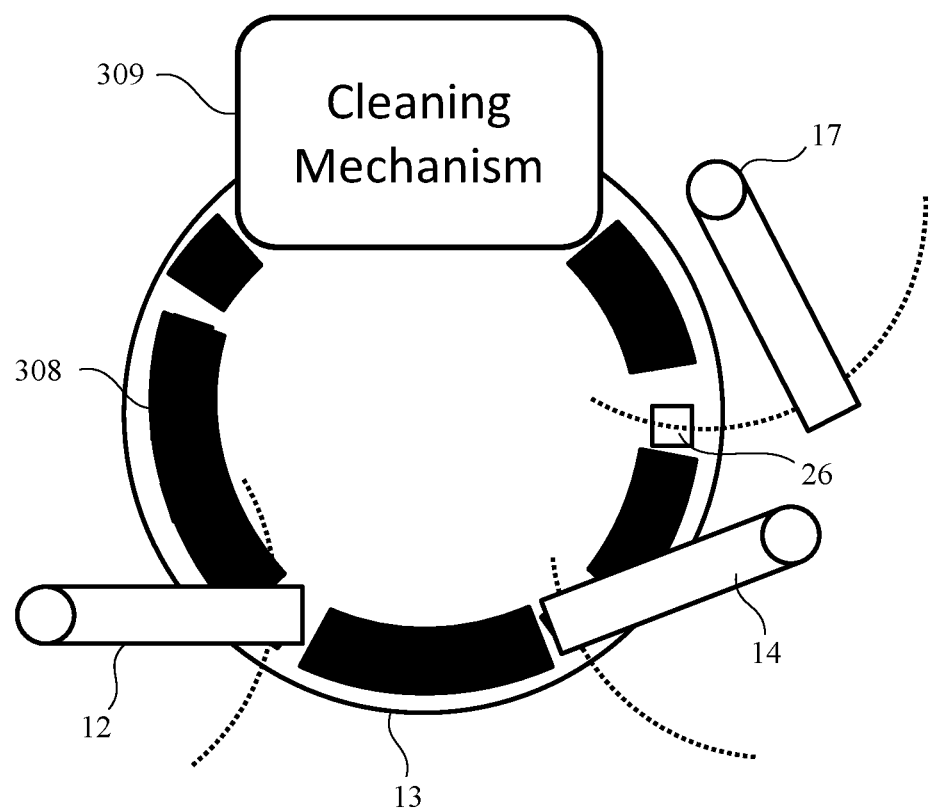

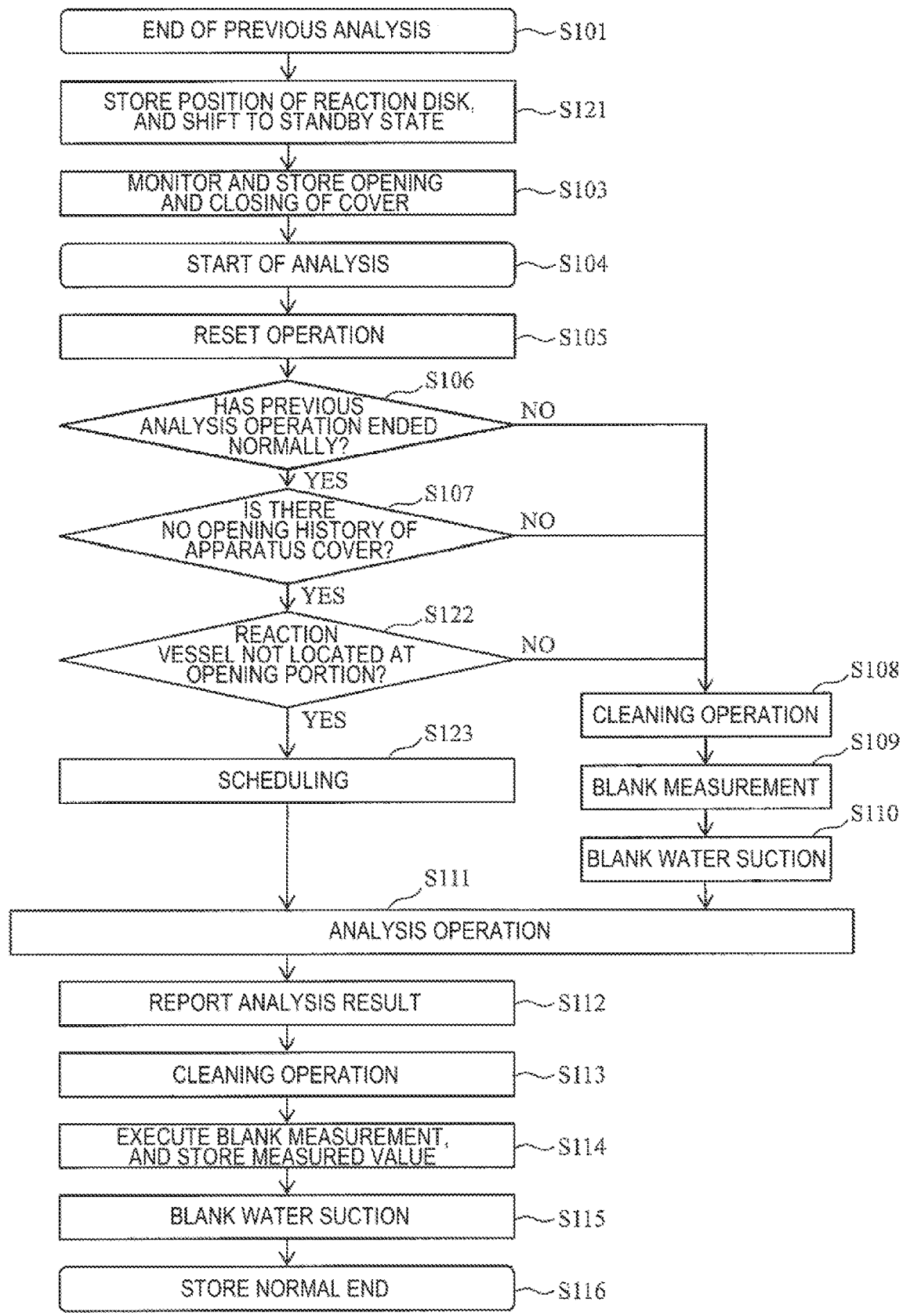
[FIG. 8]

[FIG. 9]
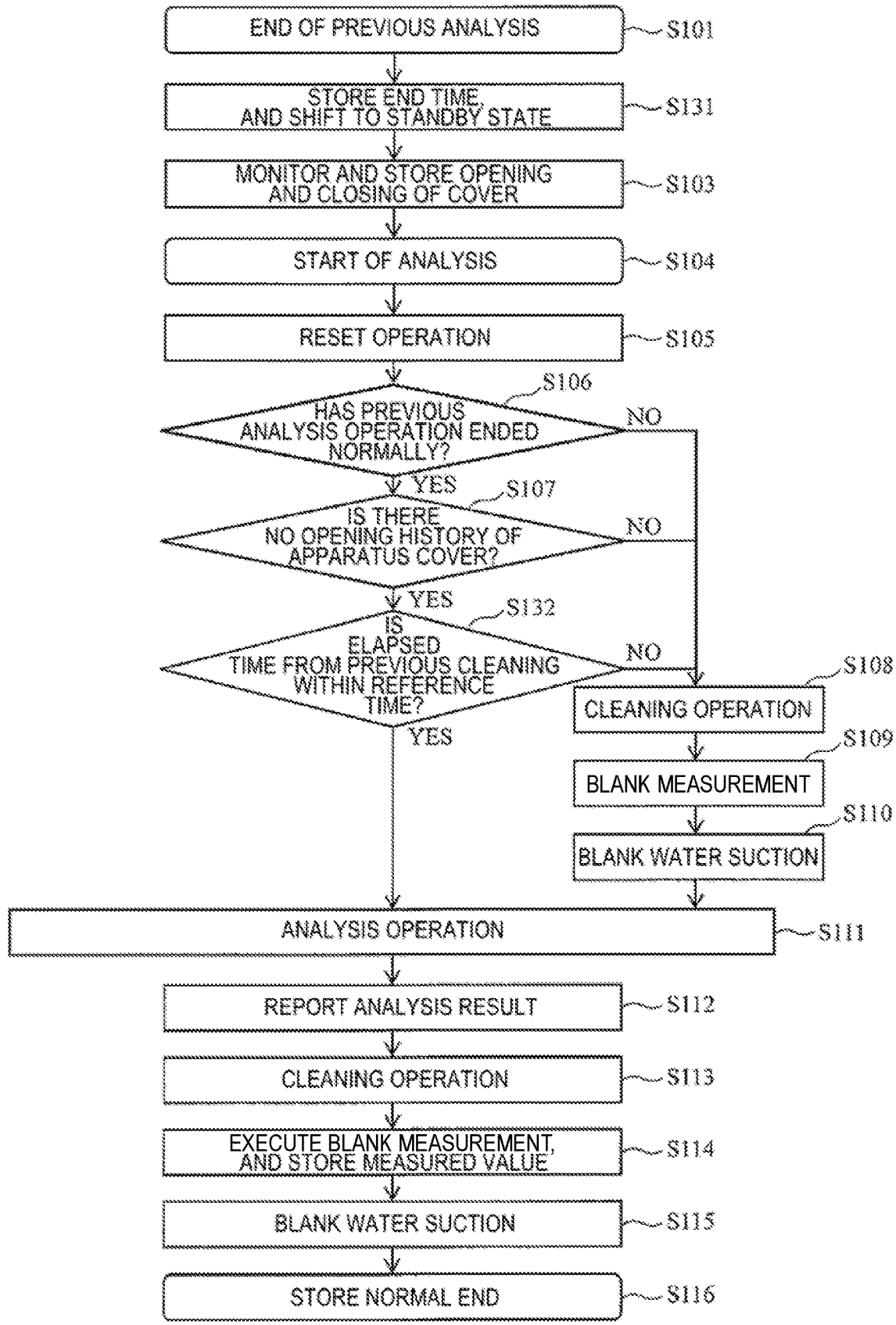

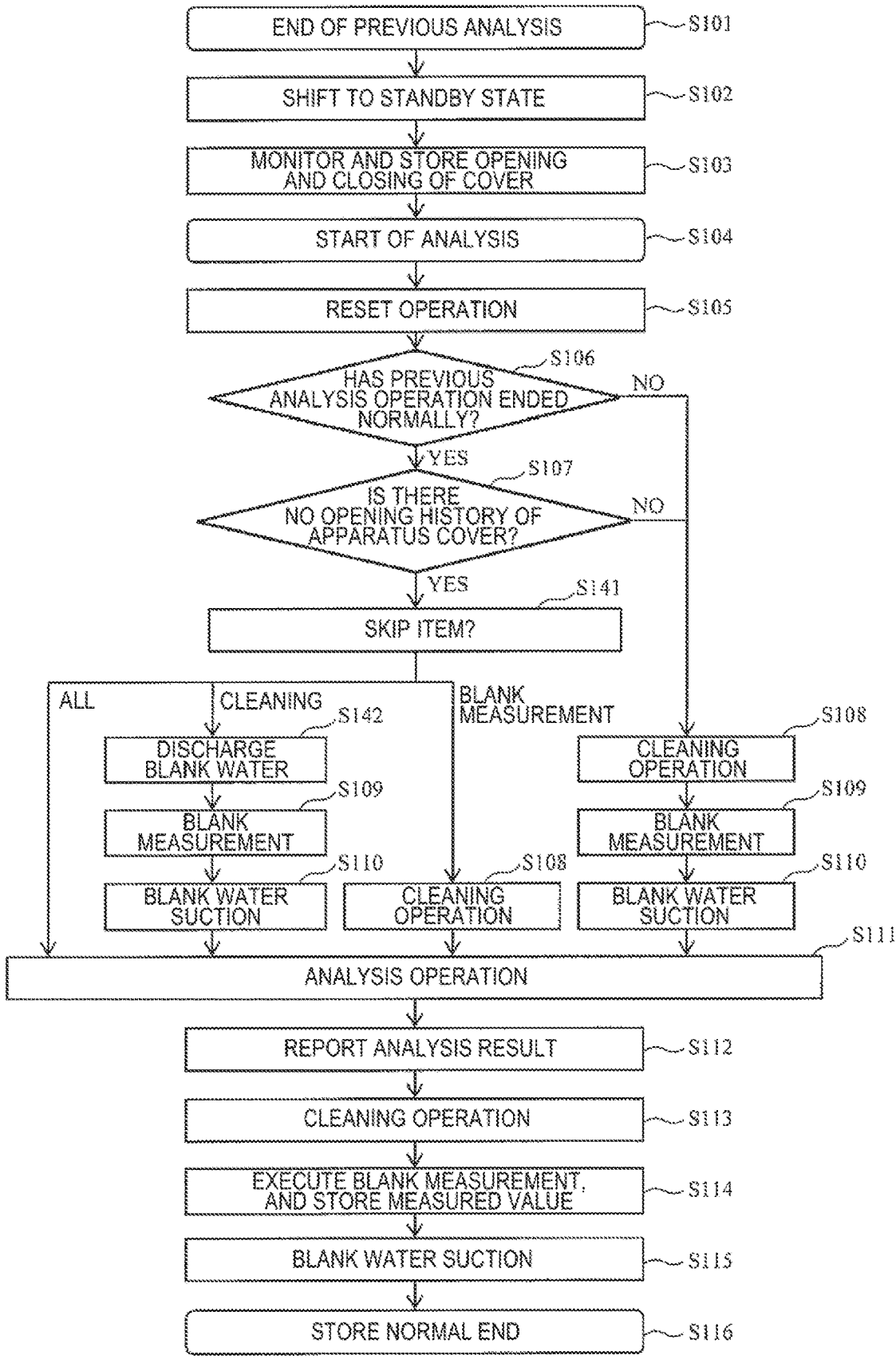
[FIG. 10]

AUTOMATED ANALYZER AND CONTROL METHOD FOR SAME

TECHNICAL FIELD

The present invention relates to an automated analyzer for analyzing a reaction solution contained in a reaction vessel, which can be cleaned to be repeatedly used, and a control method for the same.

BACKGROUND ART

An automated analyzer is known as an apparatus for analyzing components contained in a sample (hereinafter, referred to as a "sample" or a "biological sample"), such as blood or urine. The automated analyzer analyzes components of a sample by emitting light from a light source to a reaction vessel containing a reaction solution, in which a sample to be analyzed is mixed with a reagent, and measuring the amount of transmitted light or scattered light having a single wavelength or a plurality of wavelengths obtained at that time.

In the fields of biochemical examinations or hematology examinations, an automated analyzer for biochemical analysis, which is called an automated biochemical analyzer, and the like are used, and target components contained in the biological sample are quantitatively or qualitatively analyzed. In the automated biochemical analyzer, a vessel that can be repeatedly used by being cleaned by a cleaning mechanism is used as a reaction vessel for dispensing a mixed solution of a biological sample and a reagent.

If there are scratches, dirt, or mixing of foreign matter in the reaction vessel, the reliability of the analysis result is lowered, and a wrong result is output. Therefore, the automated biochemical analyzer has a function of measuring (blank measurement) transmitted light or scattered light by putting only water into the cleaned reaction vessel before the start of the analysis and notifying the operator that scratches, dirt, or mixing of foreign matter has been detected when scratches, dirt, or mixing of foreign matter is detected by comparing the measurement result with the reference value.

In particular, in an automated analyzer based on a method of measuring scattered light, the detected intensity of scattered light noticeably changes due to scratches, dirt, and mixing of foreign matter in the reaction vessel. This greatly affects the analysis result. This type of automated analyzer is also strongly affected by ambient light. For example, PTL 1 discloses a configuration in which an upper portion of a scattered light measurement unit provided in this type of automated analyzer is covered with a light shielding cover to reduce the influence of external light. In addition, PTL 2 discloses a composite type automated analyzer capable of measuring both a biochemical analysis item and a blood coagulation time item.

PTL 3 discloses a technique in which the opening and closing of an upper cover that covers a reaction vessel is monitored when an automated analyzer automatically shifts to a standby state, it is determined that mixing of foreign matter and occurrence of scratches and dirt are not possible when there is no opening and closing, and cleaning and blank measurement before the start of the analysis are skipped to shorten the time from the start of the analysis to the reporting of the analysis result.

CITATION LIST

Patent Literature

PTL 1: JP-A-2013-72799
PTL 2: WO2013/187210
PTL 3: JP-A-2009-31202

SUMMARY OF INVENTION

Technical Problem

In recent years, in the field of clinical examinations, it is required to shorten the time (turnaround time: TAT) from blood collection to sample pretreatment, analysis, and result reporting. In particular, a blood coagulation analysis for measuring the coagulability of blood is often performed in a situation requiring urgency, such as before surgery. In urgent specimen analysis, the time from the input of the sample to the reporting of the result is important. Therefore, it is necessary not only to improve the processing capacity per hour but also to start the analysis operation earlier.

Incidentally, the processing capacity required for the urgent specimen analysis at night, holidays, and the like is not high. For this reason, in this type of application, a small automated analyzer is mainly used. In a small automated analyzer, a vessel containing a sample is often placed on a turntable. In this type of automated analyzer, however, it is necessary to open and close a cover covering an upper side of a reaction disk at the time of sample introduction. Therefore, even if the automated analyzer has a function disclosed in PTL 3, if the opening and closing of the cover according to the introduction of a sample is frequent, the cleaning operation and the blank measurement before the analysis can hardly be skipped. As a result, it is not possible to shorten the TAT.

Therefore, the present invention provides a technique for shortening the TAT of an automated analyzer compared with that in the related art.

Solution to Problem

In order to solve the aforementioned problem, the present invention adopts, for example, the configuration described in the claims. This specification includes a plurality of means for solving the aforementioned problem. As an example thereof, "an automated analyzer including: a reaction disk on which a plurality of reaction vessels capable of containing a mixed solution of a sample and a reagent are placed; a first cover that covers at least a part of an upper side of the reaction disk; a second cover that is openable and closable independently of the first cover; at least one sensor that monitors opening and closing of the first cover; and a control unit that monitors a signal from the sensor and performs control to skip one or both of a cleaning operation and a blank measurement operation before analysis start in a case where there is no opening and closing of the first cover until a new analysis operation starts" is included.

This specification includes the content disclosed in Japanese Patent Application No. 2016-004721, which is the basis of priority of the present application.

Advantageous Effects of Invention

According to the present invention, since the number of executions of the cleaning operation and the blank measurement before the start of analysis is reduced, the TAT is shortened. Problems, configurations, and effects other than those described above will be clarified by the following description of the embodiments.

BRIEF DESCRIPTION OF DRAWINGS

FIG. 1 is a diagram showing the basic configuration of an automated analyzer according to Embodiment 1.

FIG. 2 is a diagram showing an example of the arrangement of an apparatus cover used in the automated analyzer according to Embodiment 1.

FIG. 3 is a flowchart showing an example of an analysis sequence according to Embodiment 1.

FIG. 4 is a graph showing an example of time allocation of the analysis sequence according to Embodiment 1.

FIG. 5 is a diagram showing an example of the arrangement of an apparatus cover used in an automated analyzer according to Embodiment 2.

FIG. 6 is a diagram showing an example of the arrangement of an apparatus cover used in an automated analyzer according to Embodiment 3.

FIG. 7 is a diagram showing an example of the arrangement of an apparatus cover used in an automated analyzer according to Embodiment 4.

FIG. 8 is a flowchart showing an example of an analysis sequence according to Embodiment 6.

FIG. 9 is a flowchart showing an example of an analysis sequence according to Embodiment 7.

FIG. 10 is a flowchart showing an example of an analysis sequence according to Embodiment 8.

DESCRIPTION OF EMBODIMENTS

Hereinafter, embodiments of the present invention will be described with reference to the diagrams. In addition, the same reference numerals are attached to components having the same functions in respective diagrams, and the explanation thereof may be omitted. The present invention is not limited to the embodiments described later, and various modifications can be made within the scope of the technical idea.

(1) Embodiment 1

(1-1) Apparatus Configuration

FIG. 1 shows the basic configuration of an automated analyzer according to the present embodiment. In the present embodiment, a composite type automated analyzer including a turntable type biochemical analysis unit and blood coagulation time analysis unit will be described. An automated analyzer 1 has a blood coagulation time analysis unit 2, a sample disk 11, a reaction disk 13, a first reagent disk 16, a second reagent disk 15, and a photometer 19 on its housing.

The blood coagulation time analysis unit 2 is configured to mainly include a sample dispensing position 18, a blood coagulation reagent dispensing mechanism 20, a blood coagulation time detecting unit 21, an optical jig magazine 22, a reaction vessel transport mechanism 23, a reaction vessel disposal port 24, and a disposable reaction vessel magazine 25. The blood coagulation time detecting unit 21 heats blood discharged to a disposable reaction vessel 28 to a predetermined temperature (for example, 37° C.), and measures the coagulation time of the blood. The reaction vessel transport mechanism 23 transports the disposable reaction vessel 28 from the disposable reaction vessel magazine 25 to the blood coagulation time detecting unit 21.

The sample disk 11 is a disk-shaped unit that can rotate clockwise or counterclockwise, and a plurality of sample vessels 27 containing samples, such as standard samples or samples to be examined, can be arranged on the circumference of the sample disk 11. The reaction disk 13 is a disk-shaped unit that can rotate clockwise or counterclockwise, and a plurality of reaction vessels 26 can be arranged on the circumference of the reaction disk 13.

The first reagent disk 16 and the second reagent disk 15 are disk-shaped units that can rotate clockwise or counterclockwise, and a plurality of reagent vessels containing a reagent that reacts with a component corresponding to each examination item contained in a sample can be arranged on the circumferences of the first reagent disk 16 and the second reagent disk 15. A cold reserving mechanism (not shown) can be provided in the first reagent disk 16 and the second reagent disk 15. When the cold reserving mechanism is provided, it is possible to cool a reagent in the reagent vessel.

A sample dispensing probe 12 is disposed between the sample disk 11 and the reaction disk 13. The sample dispensing probe 12 moves between the sample vessel 27 on the sample disk 11, the reaction vessel 26 on the reaction disk 13, and the disposable reaction vessel 28 located at the sample dispensing position 18 of the blood coagulation time analysis unit 2, thereby sucking or dispensing a sample from or to the reaction vessel at each position.

A first reagent dispensing probe 14 is disposed between the reaction disk 13 and the first reagent disk 16, and a second reagent dispensing probe 17 is disposed between the reaction disk 13 and the second reagent disk 15. Each probe moves between the reaction vessel 26 on the reaction disk 13 and a reagent vessel on the first reagent disk 16 or between the reaction vessel 26 on the reaction disk 13 and a reagent vessel on the second reagent disk 15, thereby sucking or discharging a reagent from or to each vessel.

(1-2) Configuration of Control System

Subsequently, a control system and a signal processing system provided in the automated analyzer 1 will be briefly described with reference to FIG. 1. A computer 105 communicates with a sample dispensing control unit 201, a transport mechanism control unit 202, an A/D converter (2) 203, a blood coagulation reagent dispensing control unit 204, an A/D converter (1) 205, a reagent dispensing control unit (1) 206, and a reagent dispensing control unit (2) 207 through an interface 101 to control the operation of each control unit.

The sample dispensing control unit 201 controls the dispensing operation of the sample dispensing probe 12 based on a command received from the computer 105 to dispense a sample to the disposable reaction vessel 28. The transport mechanism control unit 202 controls the driving of the reaction vessel transport mechanism 23 based on a command from the computer 105. Through this driving control, the transport mechanism control unit 202 transports the disposable reaction vessel 28 for blood coagulation analysis between the sample dispensing position 18, a reaction port 208 of the blood coagulation time detecting unit 21, the reaction vessel disposal port 24, and the disposable reaction vessel magazine 25.

The blood coagulation reagent dispensing control unit 204 controls the dispensing operation of the blood coagulation reagent dispensing mechanism 20 based on a command received from the computer 105 to dispense a reagent for blood coagulation to the disposable reaction vessel 28 moved to the reaction port 208. In this case, mixing of the reagent for blood coagulation and the sample is performed within the disposable reaction vessel 28.

Alternatively, the blood coagulation reagent dispensing control unit 204 controls the dispensing operation of the blood coagulation reagent dispensing mechanism 20 based on a command received from the computer 105. That is, the blood coagulation reagent dispensing control unit 204 controls the dispensing operation of the blood coagulation reagent dispensing mechanism 20 to dispense a pretreatment solution (mixed solution of the sample and the reagent for blood coagulation analysis; the mixed solution is generated within the reaction vessel 26) to the empty disposable reaction vessel 28. In this case, the blood coagulation reagent dispensing control unit 204 further dispenses a second reagent for blood coagulation analysis to the disposable reaction vessel 28 containing the pretreatment solution.

The reagent for blood coagulation analysis herein is disposed on the first reagent disk 16 and the second reagent disk 15. As necessary, the reagent for blood coagulation analysis is dispensed to the reaction vessel 26 on the reaction disk 13 by the first reagent dispensing probe 14 and the second reagent dispensing probe 17, and is then used for blood coagulation analysis.

The reagent dispensing control unit (1) 206 and the reagent dispensing control unit (2) 207 control the reagent dispensing operations of the first reagent dispensing probe 14 and the second reagent dispensing probe 17 based on a command received from the computer 105.

The A/D converter (1) 205 converts the photometric value of transmitted light or scattered light of the reaction solution in the reaction vessel (for biochemical analysis) 26 into a digital signal, and outputs the digital signal to the computer 105 through the interface 101. The A/D converter (2) 203 converts the photometric value of transmitted light or scattered light of the reaction solution in the disposable reaction vessel (for blood coagulation analysis) 28 into a digital signal, and outputs the digital signal to the computer 105 through the interface 101.

In the case of the present embodiment, a printer 106 used when outputting the measurement result as a report or the like, a memory 104 or an external output medium 102 that is a storage device, an input device 107 such as a keyboard used by an operator for inputting, and a display device 103 for displaying an operation screen are connected to the interface 101. As the display device 103, for example, a liquid crystal display, a CRT display, and the like are used.

(1-3) Analysis of Biochemical Items

The automated analyzer 1 analyzes biochemical items in the following procedure. First, an operator inputs examination items for each sample through the input device 107, such as a keyboard. The computer 105 controls the driving of the sample dispensing probe 12 in order to analyze the sample for the input examination items. At this time, the sample dispensing probe 12 dispenses a predetermined amount of sample from the sample vessel 27 to the reaction vessel (for biochemical analysis) 26 according to the analysis parameter.

The reaction vessel (for biochemical analysis) 26 to which the sample has been dispensed is transported by the rotation of the reaction disk 13 and stops at the reagent receiving position. The pipette nozzle of the first reagent dispensing probe 14 or the second reagent dispensing probe 17 dispenses a predetermined amount of reagent solution to the reaction vessel (for biochemical analysis) 26 according to the analysis parameter of the corresponding examination item. The sample may be dispensed either before or after dispensing the reagent.

The sample and the reagent dispensed into the reaction vessel 26 are stirred and mixed by a stirring mechanism (not shown). When the reaction vessel (for biochemical analysis) 26 containing the mixed solution (also referred to as a "reaction solution") traverses a photometric position, transmitted light or scattered light of the reaction solution is measured by the photometer 19. The measured transmitted light or scattered light is converted into data having a numerical value proportional to the amount of light by the A/D converter (1) 205, and the data is transmitted to the computer 105 through the interface 101.

The computer 105 calculates concentration data of a predetermined component contained in the sample based on the numerical value and a calibration curve measured in advance by using an analysis method designated for each examination item. The component concentration data is the analysis result of each examination item. The component concentration data is output to the printer 106 or the screen of the display device 103. In addition, before the analysis operation described above, the operator registers various parameters required for analysis and reagents and samples to be used through the operation screen of the display device 103. In addition, the operator checks the analysis result after the measurement through the operation screen on the display device 103.

(1-4) Analysis of Blood Coagulation Time Item

The automated analyzer 1 analyzes the blood coagulation time item in the following procedure. First, the operator inputs examination items for each sample through the input device 107, such as a keyboard. The computer 105 controls the driving of the reaction vessel transport mechanism 23 in order to analyze the sample for the input examination items. At this time, the reaction vessel transport mechanism 23 transports the disposable reaction vessel (for blood coagulation analysis) 28 from the disposable reaction vessel magazine 25 to the sample dispensing position 18. Then, the computer 105 controls the driving of the sample dispensing probe 12 to dispense a predetermined amount of sample from the sample vessel 27 to the disposable reaction vessel (for blood coagulation analysis) 28.

The disposable reaction vessel (for blood coagulation analysis) 28 to which the sample has been dispensed is transported to the reaction port 208 of the blood coagulation time detecting unit 21 by the reaction vessel transport mechanism 23, and is heated to a predetermined temperature (for example, 37° C.). The first reagent dispensing probe 14 dispenses a predetermined amount of reagent solution to the reaction vessel (for biochemical analysis) 26 on the reaction disk 13 according to the analysis parameter of the corresponding examination item. A constant temperature bath (not shown) is provided in the reaction disk 13, and the reagent solution dispensed to the reaction vessel (for biochemical analysis) 26 is heated to 37° C.

Then, the blood coagulation reagent dispensing mechanism 20 sucks the reagent dispensed to the reaction vessel (for biochemical analysis) 26, and heats the reagent to a predetermined temperature using a temperature increasing mechanism (not shown). Thereafter, the reagent is discharged to the disposable reaction vessel (for blood coagulation analysis) 28.

From the point in time at which the reagent is discharged, measurement of transmitted light or scattered light of light emitted to the disposable reaction vessel (for blood coagulation analysis) 28 is started. The measured transmitted light or scattered light is converted into data having a numerical value proportional to the amount of light by the A/D converter (2) 203, and the data is transmitted to the computer 105 through the interface 101.

The computer 105 calculates a time (blood coagulation time) required for blood coagulation reaction using the converted numerical value. For example, in an examination item, such as an activated partial thromboplastin time (ATPP), the blood coagulation time calculated in this manner is output as an analysis result. Here, for an examination item such as fibrinogen (Fbg), in addition to the calculated blood coagulation time, component concentration data is calculated based on a calibration curve measured in advance by using an analysis method designated for each examination item, and is output as an analysis result. The blood coagulation time or the component concentration data as an analysis result of each examination item is output to the printer 106 or the screen of the display device 103.

Before executing the measurement operation described above, the operator registers various parameters required for analysis and reagents and samples to be used through the operation screen of the display device 103. In addition, the operator checks the analysis result after the measurement through the operation screen on the display device 103.

The sample dispensing probe 12 may discharge the sample sucked from the sample vessel 27 to the reaction vessel (for biochemical analysis) 26. In this case, a solution that has been reacted with the pretreatment solution within the reaction vessel (for biochemical analysis) 26 in advance can also be dispensed to the disposable reaction vessel (for blood coagulation analysis) 28 by the dispensing probe of the blood coagulation reagent dispensing mechanism 20.

The dispensing probe of the blood coagulation reagent dispensing mechanism 20 vigorously discharges a reagent with respect to the sample previously contained in the disposable reaction vessel (for blood coagulation analysis) 28, so that the sample and the reagent in the disposable reaction vessel (for blood coagulation analysis) 28 are mixed. Stirring by such mixing is called discharge stirring. In addition, the reagent may be dispensed before the sample. In this case, the sample is mixed with the reagent due to the momentum when the sample is discharged.

(1-5) Configuration of Cover

FIG. 2 shows an example of the configuration of an apparatus cover used in the automated analyzer 1 of the present embodiment. The apparatus cover of the present embodiment is formed by two covers of a sample disk cover 301 that covers only the sample disk 11 and an entire cover 302 that covers the reaction disk 13, the first reagent disk 16, and the second reagent disk 15. The sample disk cover 301 and the entire cover 302 are independent of each other, and can be individually opened and closed.

Therefore, even in a case where sample replacement or additional work is required from the end of measurement to the start of the next measurement, it is not necessary to open the entire cover 302 that covers the upper portion of the reaction disk 13. As a result, even if sample replacement or additional work is performed, there is no possibility that foreign matter will be mixed into the reaction vessel. Therefore, since cleaning and blank measurement before the start of the analysis can be skipped, it is possible to shorten the TAT. In addition, the automated analyzer 1 has an opening and closing detection sensor 211 for detecting the opening and closing of the entire cover 302. If the opening and closing of the entire cover 302 can be detected, the opening and closing detection sensor 211 can be mounted in an arbitrary manner. In addition, the opening and closing detection sensor may also be provided on the sample disk cover 301. The output of the opening and closing detection sensor 211 is input to the computer 105 through the interface 101.

(1-6) Analysis Sequence

FIG. 3 shows an example of the analysis sequence executed by the automated analyzer 1. The analysis sequence shown in FIG. 3 is realized by controlling a program executed by the computer 105. As will be described later, the analysis sequence of the present embodiment includes an apparatus cover opening and closing monitoring function (by a sensor not shown), and the skipping of the cleaning operation and the blank measurement before the start of the analysis is executed by this function.

When control is started with a point in time at which the previous analysis ends as a base point (step S101), the computer 105 shifts the operation mode to the standby state (S102). While the computer 105 is in the standby state, the computer 105 monitors the opening and closing of the apparatus cover, and stores the monitoring result in the memory 104 if there is opening or closing (S103). In the case of the present embodiment, only the opening and closing of the entire cover 302 is monitored. However, the computer 105 may monitor the opening and closing of both the sample disk cover 301 and the entire cover 302. In this case, since the type of the opened or closed cover is also recorded in the memory 104, it can be determined which cover has been opened or closed.

When the operator gives an instruction to start the analysis operation, the computer 105 starts the analysis sequence (step S104), and performs a reset operation first (S105). Then, the computer 105 reads the previous analysis data from the memory 104, and determines whether or not the "previous analysis operation" has ended normally (S106). In a case where the "previous analysis operation" has ended normally, the computer 105 reads the opening and closing history data of the apparatus cover from the memory 104, and determines the presence or absence of "opening history" (step S107). Here, the absence of "opening history" means that the "previous analysis operation" ended normally, the reaction vessel 26 was cleaned after the analysis, and there is no possibility that foreign matter will be mixed into the reaction vessel 26.

Therefore, in a case where a positive result is obtained in step S107, the computer 105 starts the current analysis operation as it is using a blank value measured after the previous analysis (step S111). On the other hand, in a case where the "previous analysis operation" has ended normally (negative result in step S106) or in a case where there is an opening history of the apparatus cover (negative result in step S107), the computer 105 executes a cleaning operation (step S108), blank measurement (step S109), and blank water suction (step S110) in order, and then starts the analysis operation (step S111).

In any case, the computer 105 reports the analysis result after the end of the measurement (step S112). The report of the analysis result is output to the printer 106 or the screen of the display device 103. Then, the computer 105 gives an instruction to clean the reaction vessel 26 used for the measurement (step S113), and executes blank measurement and stores the measured value in the memory 104 (step S114). Then, the computer 105 gives an instruction to suck blank water (step S115), and finally stores in the memory 104 that the analysis operation has ended normally (step S116).

(1-7) Effect of Embodiment

FIG. 4 shows an example of the time allocation of the analysis sequence according to the present embodiment. In the diagram, the horizontal axis indicates time (second), and three sequence patterns are shown in the vertical direction. The uppermost sequence pattern is an example in a case where both the cleaning operation and the blank measurement are skipped, the middle sequence pattern is an example in a case where only the cleaning operation is skipped, and the lowermost sequence pattern is an example of normal operation. The normal operation means that the cleaning operation and the blank measurement shown in steps S108 to S110 in FIG. 3 are necessarily executed before the start of the analysis operation.

In the case of the automated analyzer 1 of the present embodiment, since the sample disk cover 301 and the entire cover 302 that can be independently opened and closed are provided, the entire cover 302 can be kept closed even if the sample disk cover 301 is opened to add or replace a sample. As a result, it is possible to prevent the possibility of contamination of the reaction vessel 26. Therefore, since the cleaning operation and the blank measurement can be skipped, it is possible to shorten the time from the start of the operation by the operator to the reporting of the analysis result.

(2) Embodiment 2

An automated analyzer 1 according to Embodiment 2 will be described. The automated analyzer 1 of the present embodiment has the same configuration as that of Embodiment 1 except for the configuration of the apparatus cover. FIG. 5 shows the configuration of an apparatus cover used in the present embodiment. The apparatus cover of the present embodiment is formed by two covers of a reaction disk cover 303 that covers only the reaction disk 13 and an entire cover 304 that covers at least the sample disk 11, the first reagent disk 16, and the second reagent disk 15.

However, the entire cover 304 may further cover the entire reaction disk cover 303. That is, the reaction disk 13 may be doubly covered with the reaction disk cover 303 and the entire cover 304. In addition, the entire cover 304 shown in FIG. 5 also covers the blood coagulation time analysis unit 2, but may be configured not to cover the blood coagulation time analysis unit 2.

In the case of the present embodiment, it is possible to replace or add samples and replace or add reagents without opening the reaction disk cover 303 from the end of the measurement to the start of the next measurement. Therefore, in the automated analyzer 1 of the present embodiment, it is possible to add the conditions under which the cleaning operation and the blank measurement can be skipped, compared with Embodiment 1.

Also in the case of the present embodiment, the automated analyzer 1 executes the analysis operation in the procedure shown in FIG. 3. In the case of the present embodiment, however, opening and closing of the reaction disk cover 303 is monitored, and whether or not to skip the cleaning operation and the blank measurement is determined based on the opening and closing history of the reaction disk cover 303. In the case of the present embodiment, even if the entire cover 304 is opened for replacement or addition of a reagent, the reaction disk 13 is not exposed to the outside unlike in Embodiment 1. Therefore, it is possible to shorten the time from the start of the operation by the operator to the reporting of the analysis result compared with Embodiment 1.

(3) Embodiment 3

An automated analyzer 1 according to Embodiment 3 will be described. The automated analyzer 1 of the present embodiment has the same configuration as that of Embodiment 1 except for the configuration of the apparatus cover. The apparatus cover of the present embodiment is formed by two covers of a reaction disk cover that covers the reaction disk 13 and two independent entire covers that cover the other portions.

FIG. 6 shows the configuration of an apparatus cover used in the present embodiment. The apparatus cover shown in FIG. 6 is formed by three covers of a reaction disk cover 305 that covers only apart of the reaction disk 13, an entire cover 306 that covers a left portion of the reaction disk 13 not covered with the reaction disk cover 305 and the sample disk 11, and an entire cover 307 that covers a right portion of the reaction disk 13 not covered with the reaction disk cover 305, the first reagent disk 16, and the second reagent disk 15. Any of the covers is attached to the rear side of the main body of the apparatus so as to be able to be opened and closed with the rotation axis indicated by the one-dot chain line in the diagram as its center.

In the case of the present embodiment, both or one of the entire covers 306 and 307 can be opened and closed while the reaction disk cover 305 is closed. However, in the case of opening the reaction disk cover 305, the entire covers 306 and 307 are simultaneously opened at the same time as the opening of the reaction disk cover 305. Here, a step difference is provided along the left and right edges of the reaction disk 305, and edge portions of the entire covers 306 and 307 are disposed so as to overlap the upper surface of the lower step surface.

The reaction disk cover 305 is formed of a light shielding material so that external light is not incident on the photometer 19 (that is, external light is blocked). On the other hand, since the entire covers 306 and 307 are not required to block light, the entire covers 306 and 307 are formed of a material through which light passes. Therefore, even if the entire covers 306 and 307 are not opened, the operating states of the sample disk 11, the first reagent disk 16, the second reagent disk 15, and the like can be visually checked through the entire covers 306 and 307. In the case of FIG. 6, however, since a part of the reaction disk 13 can be visually checked, the operation of the reaction disk 13 can be indirectly estimated from the visible portion.

Needless to say, also in the case of the automated analyzer 1 of the present embodiment, as in Embodiment 2, it is possible to replace or add samples and replace or add reagents without opening the reaction disk cover 305 from the end of the measurement to the start of the next measurement. As a result, it is possible to add the conditions under which the cleaning operation and the blank measurement can be skipped, compared with Embodiment 1.

Also in the case of the present embodiment, the automated analyzer 1 executes the analysis operation in the procedure shown in FIG. 3. However, the computer 105 monitors the opening and closing of the reaction disk cover 305, and determines whether or not to skip the cleaning operation and the blank measurement based on the opening and closing history of the reaction disk cover 305. Through this structure, the automated analyzer 1 of the present embodiment can shorten the time from the start of the operation by the operator to the reporting of the analysis result.

However, in the case of using the reaction disk cover 305 having the configuration shown in FIG. 6, a part of the reaction disk 13 is exposed to the outside when the entire cover 306 or 307 is opened. For this reason, in the case of using the cover shown in FIG. 6, it is preferable to provide a function of checking the reaction vessel 26 exposed to the outside when the entire cover 306 or 307 is opened and storing the checking result in the memory 104 by preparing an opening and closing detection sensor for each of the entire covers 306 and 307. Then, for the reaction vessel 26 exposed to the outside, the same processing as in the case where the reaction disk cover 305 is opened is executed.

With this function, it is possible to skip the cleaning operation and the blank measurement for the reaction vessels 26 located in the area covered with the reaction disk cover 305. As a result, it is possible to shorten the measurement time for these reaction vessels 26. In addition, the details of this processing can be realized by the same processing method (FIG. 8) as in Embodiment 6 to be described later, for example. In addition, although the reaction disk cover 305 having the configuration shown in FIG. 6 is used in the present embodiment, it is needless to say that the reaction disk cover 305 may be a cover that covers the entire reaction disk 13. The operation in the case where the reaction disk cover 305 covers the entire reaction disk 13 is the same as the operation in Embodiment 2.

(4) Embodiment 4

An automated analyzer 1 according to Embodiment 4 will be described. The automated analyzer 1 of the present embodiment has the same configuration as that of Embodiment 1 except for the configuration of the apparatus cover. The apparatus cover of the present embodiment is different from the apparatus cover of Embodiment 2 in that the reaction disk 13 is covered with one or a plurality of vessel covers. In addition, portions other than the reaction disk 13 are covered with the entire cover described in Embodiment 2.

FIG. 7 shows an example of an apparatus cover used in the present embodiment. As described above, a plurality of reaction vessels 26 are placed on the reaction disk 13 along the circumference thereof. In the case of the present embodiment, a configuration is adopted in which the upper side of the reaction vessel 26 is covered with one or a plurality of reaction vessel covers 308 except for the dispensing positions of the sample dispensing probe 12, the first reagent dispensing probe 14, and the second reagent dispensing probe 17. However, a position where the cleaning mechanism 309 is provided is not covered with the reaction vessel cover 308 either. The reaction vessel cover 308 shown in FIG. 7 has a fan shaped or an annular shape matching the shape of the reaction disk 13. In FIG. 7, a plurality of reaction vessels 26 placed on the reaction disk 13 are covered with the five reaction vessel covers 308. Needless to say, the number is an example.

In the case of a configuration including a plurality of reaction vessel covers 308, each reaction vessel cover can be attached and detached independently at positions where the upper portion of the reaction disk 13 is covered. Needless to say, for each reaction vessel cover 308, an opening and closing detection sensor (not shown) for detecting the opening and closing of the reaction vessel cover 308 is provided. The reaction vessel cover 308 may be used in combination with the entire cover 302 (FIG. 2), the reaction disk cover 303 (FIG. 5), and the reaction disk cover 305 (FIG. 6) of the respective embodiments described above.

In the case of using the reaction vessel cover 308, it is possible to prepare a large number of reaction vessels 26 for which the cleaning operation and the blank measurement before the analysis operation can be skipped even if the reaction disk cover 305 (FIG. 6) is opened, for example. In addition, in a case where the reaction vessel cover 308 is provided, it is not necessary to provide the covers described in the above embodiments.

Also in the case of the present embodiment, the automated analyzer 1 executes the analysis operation in the procedure shown in FIG. 3. However, the automated analyzer 1 of the present embodiment records the opening and closing history of the reaction vessel cover 308 in the memory 104. At this time, which reaction vessel cover 308 has been opened and closed and the opening and closing time information are also recorded. If the positional relationship between the reaction vessel cover 308 and the reaction vessel 26 on the reaction disk 13 is known, the computer 105 can determine whether or not there is a possibility of contamination in the reaction vessel 26 used for the analysis operation in step S107.

Specifically, based on whether or not the reaction vessel cover 308 is opened, the computer 105 determines whether or not the reaction vessel 26 is exposed to the outside. Then, for the reaction vessel 26 exposed to the outside, a negative result is obtained in step S107, and the cleaning operation and the like are executed. On the other hand, for the reaction vessel 26 not exposed to the outside, a positive result is obtained in step S107, and the cleaning operation and the blank measurement are skipped. In this manner, by using the automated analyzer 1 of the present embodiment, it is possible to shorten the time from the start of the operation by the operator to the reporting of the analysis result.

(5) Embodiment 5

In the above embodiments, the case where the sample vessel 27 is placed on the turntable type sample disk 11 has been described. However, an automated analyzer of a type in which a rack on which the sample vessel 27 is placed is provided in the apparatus (that is, a rack type automated analyzer) may also be used.

(6) Embodiment 6

Even in a case where the reaction vessel cover 308 (FIG. 7) is used, the dispensing positions of various probes cannot be covered with the reaction vessel cover 308. For this reason, even if there is no opening and closing of the reaction vessel cover 308, there is a possibility that foreign matter will be mixed into the reaction vessel 26 located at (or having passed through) an opening portion, such as a dispensing position, in a case where a cover that covers the entire reaction disk 13 is not provided or in a case where the cover that covers the entire reaction disk 13 is opened.

Therefore, in the automated analyzer 1 according to the present embodiment, a function of determining whether or not the reaction vessel 26 is located at an opening portion is added, so that the cleaning operation and the blank measurement are executed for the reaction vessel 26 located at (or having passed through) the opening portion and the reaction vessel 26 not located at the opening portion is preferentially used for analysis. As a result, it is possible to shorten the TAT.

FIG. 8 shows an example of the analysis sequence executed by the automated analyzer 1 according to the present embodiment. In FIG. 8, parts corresponding to those in FIG. 3 are denoted by the same reference numerals. The analysis sequence shown in FIG. 8 is realized by controlling a program executed by the computer 105. When control is started with a point in time at which the previous analysis ends as a base point (step S101), the computer 105 stores the position of the reaction disk 13 (relative position of a specific point of the reaction disk 13 with respect to the reference position on the main body side) in the memory 104, and then shifts the operation mode to the standby state (S121).

While the computer 105 is in the standby state, the computer 105 monitors the opening and closing of the apparatus cover, and stores the monitoring result in the memory 104 if there is opening or closing (step S103). In the case of the present embodiment, the opening and closing of one or a plurality of reaction vessel covers 308 is monitored. However, the computer 105 may also monitor the opening and closing of the entire cover 302 (FIG. 2) that covers the upper portion of the reaction disk 13 or the reaction disk covers 303 (FIG. 5) and 305 (FIG. 6).

When the operator gives an instruction to start the analysis operation, the computer 105 starts the analysis sequence (step S104), and performs a reset operation first (step S105). Then, the computer 105 reads the previous analysis data from the memory 104, and determines whether or not the "previous analysis operation" has ended normally (step S106). In a case where the "previous analysis operation" has ended normally, the computer 105 reads the opening and closing history data of the apparatus cover from the memory 104, and determines the presence or absence of "opening history" (step S107). Here, the absence of "opening history" means that the "previous analysis operation" ended normally, the reaction vessel 26 was cleaned after the analysis, and there is no possibility that foreign matter will be mixed into the reaction vessel 26.

In a case where a positive result is obtained in step S107, the computer 105 determines whether or not the reaction vessel 26 is located at (stopped at or having passed through) the opening portion from the position information of the reaction disk 13 in the standby state that is stored in the memory 104 (step S122). In a case where a positive result is obtained in step S122, the computer 105 performs scheduling so that the reaction vessel 26 not located at (stopped at or having passed through) the opening portion is preferentially used for measurement (step S123). The reaction vessels 26 for which cleaning and the like are performed before the start of the analysis are undoubtedly used for analysis, but analysis using these is scheduled after the use of the reaction vessel 26 not located at the opening portion.

In a case where the previous analysis operation has ended normally, the reaction vessel 26 not located at the opening portion is cleaned after the end of the analysis (step S113 at the time of previous analysis), and there is no possibility that foreign matter will be mixed thereinto since there is no opening and closing of the reaction vessel cover 308 thereafter. Accordingly, the computer 105 starts the current analysis operation as it is using a blank value measured after the end of the previous analysis operation (step S111).

On the other hand, in a case where the "previous analysis operation" has ended normally (negative result in step S106), in a case where there is a history of opening the reaction vessel cover 308 (negative result in step S107), or in the case of the reaction vessel 26 located at the opening portion (negative result in step S122), the computer 105 executes the cleaning operation (step S108), the blank measurement (step S109), and the blank water suction (step S110) in order, and then starts the analysis operation (step S111). The cleaning and the like herein are executed for all the reaction vessels 26 in the case of a negative result in step S106 and a negative result in step S107, and executed for only the corresponding reaction vessel 26 in the case of a negative result in step S122.

In any case, the computer 105 reports the analysis result after the end of the measurement (step S112). The report of the analysis result is output to the printer 106 or the screen of the display device 103. Then, the computer 105 gives an instruction to clean the reaction vessel 26 used for the measurement (step S113), and executes blank measurement and stores the measured value in the memory 104 (step S114). Then, the computer 105 gives an instruction to suck blank water (step S115), and finally stores in the memory 104 that the analysis operation has ended normally (step S116).

By using the automated analyzer 1 according to the present embodiment, since it is possible to reliably prevent the reaction vessel 26 located at the opening portion from being used for measurement, both the reliability of the measurement result and the analysis result and the shortening of the TAT can be achieved. In addition, the processing operation shown in FIG. 7 can also be applied to the processing operation of the automated analyzer 1 (Embodiment 3) using the reaction disk cover 305 having the configuration shown in FIG. 6. In this case, the reaction vessel 26 located at the opening portion may be read as the reaction vessel 26 exposed to the outside by opening the entire cover 306 or 307.

(7) Embodiment 7

In the structure described in the above embodiment, in a case where it is determined that there is no opening and closing of the cover covering the upper side of the reaction disk 13 or the reaction vessel 26 or in a case where it is determined that the reaction vessel 26 is not located at the opening portion, the analysis operation is necessarily started without cleaning the reaction vessel 26. However, even if there is no opening and closing of the cover from the time when the previous analysis operation has ended normally to the start of the operation, in a case where a long time has passed from the end of the previous analysis, there is a possibility that foreign matter will be mixed through a gap or the like of the unsealed cover. For this reason, the cleaning operation and the blank measurement are required.

FIG. 9 shows an example of the analysis sequence executed by the automated analyzer 1 according to the present embodiment. In FIG. 9, parts corresponding to those in FIG. 3 are denoted by the same reference numerals. The analysis sequence shown in FIG. 9 is realized by controlling a program executed by the computer 105. When control is started with a point in time at which the previous analysis ends as a base point (step S101), the computer 105 stores the end time of the analysis operation in the memory 104, and then shifts the operation mode to the standby state (S131).

While the computer 105 is in the standby state, the computer 105 monitors the opening and closing of the apparatus cover, and stores the monitoring result in the memory 104 if there is opening or closing (step S103). When the operator gives an instruction to start the analysis operation, the computer 105 starts the analysis sequence (step S104), and performs a reset operation first (step S105). Then, the computer 105 reads the previous analysis data from the memory 104, and determines whether or not the "previous analysis operation" has ended normally (step S106). In a case where the "previous analysis operation" has ended normally, the computer 105 reads the opening and closing history data of the apparatus cover from the memory 104, and determines the presence or absence of "opening history" (step S107).

In a case where a positive result is obtained in step S107, the computer 105 reads the previous analysis end time from the memory 104 to calculate the elapsed time, and determines whether or not the calculated elapsed time is within a predetermined reference time (step S132). A case where a positive result is obtained in step S132 means that the "previous analysis operation" has ended normally, the reaction vessel 26 is cleaned after the analysis, and the elapsed time is within the reference time and accordingly there is no possibility that foreign matter will be mixed into the reaction vessel 26.

Therefore, in a case where a positive result is obtained in step S132, the computer 105 starts the analysis operation as it is using a blank value measured after the previous analysis that is stored in the memory 104 (step S111). Needless to say, as in steps S122 and S123 (FIG. 8) described in Embodiment 6, all the reaction vessels 26 located at the opening portion may be specified from the position information of the reaction disk 13 in the standby state, and scheduling according to the position of the reaction vessel 26 may be performed at the same time.

On the other hand, in a case where the "previous analysis operation" has ended normally (negative result in step S106), or in a case where there is a history of opening the reaction vessel cover 308 (negative result in step S107), or in a case where the elapsed time exceeds the reference time (negative result in step S132), the computer 105 executes the cleaning operation (step S108), the blank measurement (step S109), and the blank water suction (step S110) in order, and then starts the analysis operation (step S111).

In any case, the computer 105 reports the analysis result after the end of the measurement (step S112). The report of the analysis result is output to the printer 106 or the screen of the display device 103. Then, the computer 105 gives an instruction to clean the reaction vessel 26 used for the measurement (step S113), and executes blank measurement and stores the measured value in the memory 104 (step S114). Then, the computer 105 gives an instruction to suck blank water (step S115), and finally stores in the memory 104 that the analysis operation has ended normally (step S116).

By using the automated analyzer 1 according to the present embodiment, it is possible to avoid the possibility of a lowering in the measurement accuracy due to mixing of foreign matter in consideration of the elapsed time from the time when the previous analysis operation has ended normally to the start of the operation. Therefore, the acquisition of a more reliable analysis result and the shortening of the TAT can be achieved.

(8) Embodiment 8

In the above embodiments, the case where the cleaning operation and the blank measurement are skipped uniformly has been described. In the present embodiment, however, a case where the operator can select an item to be skipped or a case where the computer 105 automatically selects an item to be skipped according to the analysis item will be described. Even if both the cleaning operation and the blank measurement are not skipped, it is possible to shorten the TAT compared with the case of the normal operation, as shown in FIG. 4.

FIG. 10 shows an example of the analysis sequence executed by the automated analyzer 1 according to the present embodiment. In FIG. 10, parts corresponding to those in FIG. 3 are denoted by the same reference numerals. The analysis sequence shown in FIG. 10 is realized by controlling a program executed by the computer 105. In the case of the present embodiment, in a case where a positive result is obtained in step S107, skip item selection processing is executed (step S141). The skip item is selected through an operator's input on the operation screen displayed on the display device 103, and the computer 105 receives the operator's selection operation.

In the case of the present embodiment, the operator can select one among three of all skipping (both the cleaning operation and the blank measurement), skipping of cleaning operation, and skipping of blank measurement. In a case where all skipping is selected in step S141, the computer 105 starts the analysis operation immediately as in the analysis sequence shown in FIG. 3. On the other hand, in a case where skipping of cleaning operation is selected in step S141, the computer 105 executes discharging of blank water (step S142), blank measurement (step S109), and blank water suction (step S110) in order, and then starts the analysis operation. In addition, in a case where skipping of blank measurement is selected in step S141, the computer 105 starts the analysis operation immediately after executing the cleaning operation (step S108) on the reaction vessel 26.

In FIG. 10, the case where three types of skips can be selected has been described. However, the operation that can be skipped is not limited thereto. For example, selection without skipping is also possible. In addition, the computer 105 may determine whether or not to skip automatically according to the analysis item. For example, in the coagulation time item in a composite type automated analyzer or the analysis of electrolytes using an ion selective electrode (ISE) method, even in a case where the reaction vessel 26 is used, no blank value is required since light measurement using the reaction vessel 26 is not performed, and the blank measurement can be skipped without fail if there is no opening and closing of the apparatus cover.

In addition, in an item for measuring short wavelength light that is easily affected by the contamination of the reaction vessel 26 and an item for measuring scattered light that is easily affected by scratches, it is also possible to make a selection to necessarily execute the cleaning operation and the measurement of a blank value.

(9) Embodiment 9

In the cleaning operation of the reaction vessel 26, water is sucked last. However, it is not always possible to completely remove moisture. For this reason, in the reaction vessel 26 for which the cleaning operation has been performed, the analysis is started in a state in which a substantially constant amount of water remains in the vessel. On the other hand, in a case where the elapsed time from the end time of the previous analysis operation is long, residual water disappears due to evaporation of water. Therefore, in the case of starting the analysis operation as it is using the reaction vessel 26 for which the cleaning operation or the like is skipped as in the embodiments described above, the inside of the vessel is dry. However, in the reaction vessel 26 cleaned immediately before, there is a difference that the inside of the vessel is wet. This difference strictly means that the amount of thinning of a reagent or a sample changes depending on skipping, and variations may occur in the analysis result.

In the present embodiment, therefore, in order to make the state of the reaction vessel 26 used for the analysis operation the same, also in the reaction vessel 26 which is a target of the skip operation, water discharge and suction operations are executed before the start of the analysis operation. Even if only water discharge and suction are executed immediately before the analysis operation, it is possible to shift to the analysis operation in a short time unlike in the execution of the cleaning operation. In addition, as described above, since it is possible to make the state of the reaction vessel 26 the same regardless of the presence or absence of skipping, it is possible to shorten the TAT while maintaining high analytical reproducibility.

(10) Other Embodiments

The present invention is not limited to the embodiments described above, but includes various modifications. For example, the above embodiments have been described in detail in order to explain the present invention in an easy-to-understand manner, and all the configurations described above do not necessarily need to be provided. For example, monitoring of the opening and closing of the cover in step S103 may also be executed during the execution of the analysis operation. In addition, a part of one embodiment can be replaced with the configuration of another embodiment. In addition, the configuration of another embodiment can be added to the configuration of one embodiment. In addition, for a part of the configuration of each embodiment, a part of the configuration of another embodiment can be added, deleted, or replaced.

In addition, the above-described configurations, functions, processing units, processing means, and the like may be realized by hardware, for example, by designing some or all of these with an integrated circuit or the like. In addition, the above-described configurations, functions, and the like may be realized by interpreting and executing a program for realizing the respective functions by the processor (that is, by software). Information, such as a program, a table, and a file for realizing the respective functions can be stored in a storage device, such as a memory, a hard disk, and a solid state drive (SSD), or a storage medium, such as an IC card, an SD card, and a DVD. In addition, the control lines or the information lines indicate those considered to be necessary for the explanation, and do not indicate all control lines or information lines necessary for the product. In practice, it may be considered that almost all the configurations are connected to each other.

REFERENCE SIGNS LIST

1: automated analyzer
2: blood coagulation time analysis unit
11: sample disk
12: sample dispensing probe
13: reaction disk
14: first reagent dispensing probe
15: second reagent disk
16: first reagent disk
17: second reagent dispensing probe
18: sample dispensing position
19: photometer
20: blood coagulation reagent dispensing mechanism
21: blood coagulation time detecting unit
22: optical jig magazine
23: reaction vessel transport mechanism
24: reaction vessel disposal port
25: disposable reaction vessel magazine
26: reaction vessel
27: sample vessel
28: disposable reaction vessel
101: interface
102: external output medium
103: display device
104: memory
105: computer
106: printer
107: input device
201: sample dispensing control unit
202: transport mechanism control unit
203: A/D converter (2)
204: blood coagulation reagent dispensing control unit
205: A/D converter (1)
206: reagent dispensing control unit (1)
207: reagent dispensing control unit (2)
208: reaction port
211: opening and closing detection sensor
301: sample disk cover
302: entire cover
303: reaction disk cover
304: entire cover
305: reaction disk cover
306: entire cover
307: entire cover
308: reaction vessel cover All publications, patents and patent applications cited in this specification are incorporated herein by reference in their entirety.

The invention claimed is:

1. An automated analyzer, comprising:
a reaction disk on which a plurality of reaction vessels capable of containing a mixed solution of a sample and a reagent are placed, wherein the reaction vessels can be repeatedly used by being cleaned;
a sample disk or a sample rack on which one or more sample vessels containing samples are placed;
a first reagent disk that holds a plurality of reagent vessels containing a reagent;
a second reagent disk that holds a plurality of reagent vessels containing a reagent;
a photometer that performs blank measurement operations of the reaction vessels;
a cleaning mechanism that cleans the reaction vessels;
a first cover that only covers the reagent disk, wherein the first cover includes a plurality of reaction vessel covers arranged in an annular shape matching a shape of the reaction disk, the first cover covering at least a part of an upper side of the reaction disk, wherein the part of the upper side of the reaction disk that is not covered by the first cover includes at least one of a position where a sample or a reagent is dispensed to the reaction vessels and a position where the cleaning mechanism is provided, and wherein the first cover is openable and closable;
a second cover that covers portions of the automatic analyzer other than the reaction disk cover, wherein the portions include at least the sample disk, the first reagent disk, and the second reagent disk, and wherein the second cover is operable and closable independently of the first cover;
at least one sensor that monitors opening and closing of the first cover; and
a control unit that performs operation control for each portion of the automated analyzer,
wherein the control unit monitors a signal from the sensor and, based on the signal, the control unit determines whether a reaction vessel of the plurality of reaction vessels stopped at or has passed through a position of the reaction disk that is not covered by the first cover after a cleaning operation and a blank measurement operation of the reaction vessel are performed and a previous analysis operation ended normally and until a new analysis operation starts,
wherein, in a case where there is no opening and closing of the first cover after the previous analysis operation ended normally until the new analysis operation starts:
the control unit performs control to skip one or both of the cleaning operation and the blank measurement operation before analysis start for the reaction vessel that did not stop at or has not passed through the position of the reaction disk that is not covered by the first cover; and the control unit performs control not to skip the cleaning operation and the blank measurement operation before analysis start for the reaction vessel that stopped at or has passed through the position of the reaction disk that is not covered by the first cover, and wherein, in a case where there is opening and closing of the first cover after the previous analysis operation ended normally until the new analysis operation starts, the control unit performs control not to skip the cleaning operation and the blank measurement operation before analysis start also for the reaction vessel that did not stop at or has not passed through the position of the reaction disk that is not covered by the first cover.

2. The automated analyzer according to claim wherein the one or more reaction vessel covers are disposed so as to directly cover at least one of the reaction vessels placed on the reaction disk.

3. The automated analyzer according to claim 1, wherein the control unit measures and stores a time from normal end of previous analysis operation to start of next analysis, and performs control not to skip the cleaning operation and the blank measurement operation before the analysis start in a case where the measured time is longer than a threshold value set in advance, for the reaction vessel that did not stop at or has not passed through the position of the reaction disk that is not covered by the first cover even in the case where there is no opening and dosing of the first cover.

4. The automated analyzer according to claim 1, wherein the control unit performs control to use the reaction vessel that did not stop at or has not passed through the position of the reaction disk that is not covered by the first cover preferentially for analysis.

5. The automated analyzer according to claim 1, wherein the control unit controls whether or not to skip one or both of the cleaning operation and the blank measurement operation according to operator's setting or an analysis item even in the case where there is no opening and closing of the first cover.

6. The automated analyzer according to claim 1, wherein, even in the case where there is no opening and closing of the first cover that covers an upper portion of the reaction disk, the control unit performs control to start analysis atter executing only water discharge and suction with respect to the reaction vessel before start of the new analysis operation.

7. A control method for an automated analyzer including:

a reaction disk on which a plurality of reaction vessels capable of containing a mixed solution of a sample and a reagent are placed, wherein the reaction vessels can be repeatedly used by being cleaned;

a sample disk or a sample rack on which one or more sample vessels containing samples are placed;

a first reagent disk that holds a plurality of reagent vessels containing a reagent;

a second reagent disk that holds a plurality of regent vessels containing a reagent;

a photometer that performs blank measurement operations of the reaction vessels;

a cleaning mechanism that cleans the reaction vessels;

a first cover that only covers the reagent disk, wherein the first cover includes a plurality of reaction vessel covers arranged in an annular shape matching a shape of the reaction disk, the first cover covering at least a part of an upper side of the reaction disk, wherein the part of the upper side of the reaction disk that is not covered by the first cover includes at least one of a position where a sample or a reagent is dispensed to the reaction vessels and a position where a cleaning mechanism is provided, and wherein the first cover is openable and closable;

a second cover that covers portions of the automatic analyzer other than the reaction disk cover, wherein the portions include at least the sample disk, the first reagent disk, and the second reagent disk, and wherein the second cover is openable and closable independently of the first cover;

at least one sensor that monitors opening and closing of the first cover; and a control unit that controls an operation of the automated analyzer, the control unit executing the control method comprising:

a step of monitoring a signal from the sensor and determining whether or not there is opening and closing of the first cover after a cleaning operation and a blank measurement operation of the reaction vessels are performed and a previous analysis operation ended normally until a new analysis operation starts;

a step of determining whether a reaction vessel of the plurality of reaction vessels stopped at or has passed through a position that is not covered by the first cover after a cleaning operation and a blank measurement operation of the reaction vessel are performed and the previous analysis operation ended normally and until the new analysis operation starts, and a step of, in a case where there is no opening and closing of the first cover after the previous analysis operation ended normally until the new analysis operation starts:

performing control to skip one or both of a cleaning operation and a blank measurement operation before analysis start for the reaction vessel that did not stop at or has not passed through the position of the reaction disk that is not covered by the first cover; and performing control not to skip the cleaning operation and the blank measurement operation before analysis start for the reaction vessel that stopped at or has passed through the position of the reaction disk that is not covered by the first cover, and in a case where there is opening and closing of the first cover after the previous analysis operation ended normally until the new analysis operation starts, performing control not to skip the cleaning operation and the blank measurement operation before analysis start also for the reaction vessel that did not stop at or has not passed through the position of the reaction disk that is not covered by the first cover.

8. The control method according to claim 7, wherein the control unit further executes:

a step of measuring and storing a time from normal end of previous analysis operation to start of next analysis; and a step of performing control not to skip the cleaning operation and the blank measurement operation before the analysis start in a case where the measured time is longer than a threshold value set in advance, for the reaction vessel that did not stop at or has not passed through the position of the reaction disk that is not covered by the first cover and even in the case where there is no opening and closing of the first cover.

9. The control method for an automated analyzer according to claim 7, wherein the control unit further executes a step of controlling whether or not to skip one or both of the cleaning operation and the blank measurement operation according to operator's setting or an analysis item even in the case where there is no opening and closing of the first cover.

10. The control method for an automated analyzer according to claim 7,
wherein even in the case where there is no opening and closing of the first cover that covers an upper portion of the reaction disk, the control unit further executes a step of performing control to start analysis after executing only water discharge and suction with respect to the reaction vessel before start of the new analysis operation.

11. An automated analyzer, comprising:
a reaction disk on which a plurality of reaction vessels capable of containing a mixed solution of a sample and a reagent are placed, wherein the reaction vessels can be repeatedly used by being cleaned;
a sample disk or a sample rack on which one or more sample vessels containing samples are placed;
a first reagent disk that holds a plurality of reagent vessels containing a reagent;
a second reagent disk that holds a plurality of regent vessels containing a reagnet;
a photometer that performs bank measurement operations of the reaction vessels;
a cleaning mechanism that deans the reaction vessels;
a first cover that only covers the reagent disk, wherein the first cover includes a plurality of reaction vessel covers arranged in an annular shape matching a shape of the reaction disk, the first cover covering at least a part of an upper side of the reaction disk, wherein the part of the upper side of the reaction disk that is not covered by the first cover includes at least one of a position where a sample or a reagent is dispensed to the reaction vessels and a position where the cleaning mechanism is provided;
a second cover that covers portions of the automatic analyzer other than the reaction disk clover, wherein the portions include at least the sample disk the first reagent disk and the second reagent disk; and
a control unit that performs operation control for each portion of the automated analyzer,
wherein the control unit determines whether a reaction vessel of the plurality of reaction vessels stopped at or has passed through a position that is not covered by the first cover after a cleaning operation and a blank measurement operation of the reaction vessel are performed and a previous analysis operation ended normally and until a new analysis operation starts,
and wherein, after the previous analysis operation ended normally until the new analysis operation starts:
the control unit performs control to skip one or both of a cleaning operation and a blank measurement operation before analysis start for the reaction vessel that did not stop at or has not passed through the position of the reaction disk that is not covered by the first cover; and
the control unit performs control not to skip the cleaning operation and the blank measurement operation before analysis start for the reaction vessel that stopped at or has passed through the position of the reaction disk that is not covered by the first cover.

12. The automated analyzer according to claim 11,
wherein the control unit performs control to use the reaction vessel that did not stop at or has not passed through the position of the reaction disk that is not covered by the first cover preferentially for analysis.

13. An automated analyzer, comprising:
a reaction disk on which a plurality of reaction vessels capable of containing a mixed solution of a sample and a reagent are placed, wherein the reaction vessels can be repeatedly used by being cleaned;
a sample disk or a sample rack on which one or more sample vessels containing samples are placed;
a first reagent disk that holds a plurality of reagent vessels containing a reagent;
a second reagent disk that holds a plurality of regent vessels containing a reagent;
a photometer that performs blank measurement operations of the reaction vessels;
a cleaning mechanism that cleans the reaction vessels;
a first cover that only covers the reagent disk, wherein the first cover includes a plurality of reaction vessel covers arranged in an annular shape matching a shape of the reaction disk, the first cover covering at least a part of an upper side of the reaction disk, wherein the part of the upper side of the reaction disk that is not covered by the first cover includes at least one of a position where a sample or a reagent is dispensed to the reaction vessels and a position where the cleaning mechanism is provided is not covered by the first cover;
a second cover that covers portions of the automatic analyzer other than the reaction disk cover, wherein the portions include at least the sample disk, the first reagent disk, and the second reagent disk; and
a control unit that performs operation control for each portion of the automated analyzer, wherein:
the control unit determines whether a reaction vessel of the plurality of reaction vessels stopped at or has passed through a position that is not covered by the first cover after a cleaning operation and a blank measurement operation of the reaction vessel are performed and a previous analysis operation ended normally and until a new analysis operation starts;
the control unit performs control to use the reaction vessel that did not stop at and has not passed through the opening portion preferentially for the new analysis by skipping one or both of a cleaning operation and a blank measurement operation of the reaction vessel before analysis start; and
the control unit performs control not to skip one or both of the cleaning operation and the blank measurement operation before analysis start for the reaction vessel that stopped at or has passed through the position of the reaction disk that is not covered by the first cover and use them for the new analysis after all the reaction vessels that did not stop at and have not passed through the position of the reaction disk that is not covered by the first cover are used for the new analysis.

* * * * *